US010076649B2

(12) United States Patent
Gilbert et al.

(10) Patent No.: US 10,076,649 B2
(45) Date of Patent: Sep. 18, 2018

(54) DELIVERY SYSTEM FOR HOLLOW MICRONEEDLE ARRAYS

(75) Inventors: Thomas J. Gilbert, St. Paul, MN (US); Chin-Yee Ng, Oakdale, MN (US); Scott A. Burton, Woodbury, MN (US); Michael C. Molinet, Palo Alto, CA (US); Robert A. Harkins, Savage, MN (US); Bernard A. Gonzalez, St. Paul, MN (US); Larry A. Schleif, Monticello, MN (US); Patrick J. Young, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 35 days.

(21) Appl. No.: 14/342,554

(22) PCT Filed: Sep. 6, 2012

(86) PCT No.: PCT/US2012/053908
§ 371 (c)(1),
(2), (4) Date: Mar. 4, 2014

(87) PCT Pub. No.: WO2013/036602
PCT Pub. Date: Mar. 14, 2013

(65) Prior Publication Data
US 2014/0243786 A1 Aug. 28, 2014

Related U.S. Application Data

(60) Provisional application No. 61/531,843, filed on Sep. 7, 2011.

(51) Int. Cl.
*A61M 37/00* (2006.01)
*A61M 5/142* (2006.01)
*A61M 5/145* (2006.01)
*A61M 5/158* (2006.01)

(52) U.S. Cl.
CPC .... *A61M 37/0015* (2013.01); *A61M 5/14248* (2013.01); *A61M 5/1454* (2013.01); *A61M 2005/1585* (2013.01); *A61M 2037/003* (2013.01); *A61M 2037/0023* (2013.01); *A61M 2037/0061* (2013.01)

(58) Field of Classification Search
CPC .. A61M 2005/1585; A61M 2037/0023; A61M 2037/003; A61M 2037/0061; A61M 37/0015; A61M 5/14248; A61M 5/1454
See application file for complete search history.

(56) References Cited

U.S. PATENT DOCUMENTS

| 6,918,525 B2 | 7/2005 | Marks |
| 7,097,631 B2 | 8/2006 | Trautman et al. |
| 7,250,037 B2 | 7/2007 | Shermer et al. |

(Continued)

FOREIGN PATENT DOCUMENTS

| WO | WO 2004/098684 | 11/2004 |
| WO | WO 2005/018705 | 3/2005 |

(Continued)

*Primary Examiner* — Imani Hayman

(57) ABSTRACT

Systems and methods for delivering microneedles to a patient's skin are described. In one aspect, a system for delivering a microneedle array to a patient's skin surface is provided. The system includes a delivery apparatus with a housing, and an infusion device detachably received in the housing.

30 Claims, 7 Drawing Sheets

(56) References Cited

U.S. PATENT DOCUMENTS

| | | | |
|---|---|---|---|
| 7,252,651 B2* | 8/2007 | Haider | A61M 5/2033 604/137 |
| 2002/0099356 A1 | 7/2002 | Unger et al. | |
| 2003/0199823 A1 | 10/2003 | Bobroff et al. | |
| 2005/0065466 A1* | 3/2005 | Vedrine | A61M 5/14248 604/93.01 |
| 2006/0095061 A1 | 5/2006 | Trautman et al. | |
| 2006/0229559 A1 | 10/2006 | Marano-Ford et al. | |
| 2007/0021717 A1 | 1/2007 | Gabel et al. | |
| 2008/0009825 A1 | 1/2008 | Ringsred et al. | |
| 2008/0015494 A1 | 1/2008 | Santini, Jr. et al. | |
| 2008/0039805 A1 | 2/2008 | Frederickson et al. | |
| 2009/0259176 A1* | 10/2009 | Yairi | A61M 5/14248 604/67 |
| 2010/0222743 A1 | 9/2010 | Frederickson et al. | |
| 2011/0060289 A1 | 3/2011 | Ethelfeld | |
| 2011/0172609 A1 | 7/2011 | Moga et al. | |
| 2011/0172637 A1 | 7/2011 | Moga et al. | |
| 2011/0172638 A1 | 7/2011 | Moga et al. | |
| 2011/0172639 A1 | 7/2011 | Moga et al. | |
| 2011/0172645 A1 | 7/2011 | Moga et al. | |
| 2011/0213335 A1 | 9/2011 | Burton et al. | |
| 2012/0089118 A1 | 4/2012 | Deasey et al. | |
| 2012/0109066 A1* | 5/2012 | Chase | A61M 5/14248 604/173 |

FOREIGN PATENT DOCUMENTS

| | | |
|---|---|---|
| WO | WO 2005/123173 | 12/2005 |
| WO | WO 2007/002521 | 1/2007 |
| WO | WO 2011/014514 | 2/2011 |
| WO | WO 2013/055638 | 4/2013 |

* cited by examiner

DELIVERY SYSTEM FOR HOLLOW MICRONEEDLE ARRAYS

CROSS REFERENCE TO RELATED APPLICATIONS

This application is a national stage filing under 35 U.S.C. 371 of PCT/2012/053908, filed Sep. 6, 2012, claims the benefit of U.S. Provisional Patent Application No. 61/531,843, filed Sep. 7, 2011, which is incorporated herein by reference in its entirety.

SUMMARY

In one aspect, the present disclosure provides a system for delivering a microneedle array to a patient's skin surface, the system comprising: a delivery apparatus including a housing; and an infusion device detachably received in the housing. The infusion device includes a reservoir having a fluid therein and an openable end including a first major surface, a fluid pathway proximate the openable end, a first stored energy device proximate the reservoir actuatable to apply energy in a direction perpendicular to the first major surface, and an attachment surface and an array of hollow microneedles coupled to a portion of the attachment surface, wherein the pathway is in fluid communication with the hollow microneedles.

In another aspect, the present disclosure provides a method comprising providing a delivery apparatus including a housing; and an infusion device detachably received in the housing. The infusion device includes a reservoir having a fluid therein and an openable end including a first major surface, a fluid pathway proximate the openable end, a first stored energy device proximate the reservoir actuatable to apply energy in a direction perpendicular to the first major surface, and an attachment surface and an array of hollow microneedles coupled to a portion of the attachment surface, wherein the pathway is in fluid communication with the hollow microneedles. The method further comprises displacing the infusion device in a direction substantially perpendicular to the major plane of the array; establishing fluid communication between the openable end of the reservoir and the pathway; detaching the infusion device from the housing; and forcing fluid from the reservoir into the microneedle array through the pathway and into the skin.

In yet another aspect, the present disclosure provides a method for delivering a hollow microneedle array to a patient's skin surface. The method comprises providing a delivery apparatus including a housing; and an infusion device detachably received in the housing. The infusion device includes a reservoir having a fluid therein and an openable end including a first major surface, a fluid pathway proximate the openable end, a first stored energy device proximate the reservoir actuatable to apply energy in a direction perpendicular to the first major surface. The infusion device further includes an attachment surface and an array of hollow microneedles coupled to a portion of the attachment surface, wherein the pathway is in fluid communication with the hollow microneedles. The method further comprises placing a surface of the housing proximate a patient's skin surface; displacing the infusion device in a direction perpendicular to the major plane of the array; adhering a portion of the infusion device to the skin surface; establishing fluid communication between the openable end of the reservoir and the pathway, establishing fluid communication between the reservoir and the dermis and forcing fluid from the reservoir into the microneedle array through the pathway. The method further includes decoupling the housing from the infusion device, wherein the infusion device remains on the skin surface during the period of treatment.

As used herein, an "infusion device" refers to an integrated device capable of delivering or extracting a fluid over a certain period and is not limited to devices intended solely for an infusion. Accordingly, an infusion device may be used, for example, for injecting fluid into the dermis or extracting fluid from tissue.

As used herein, "hollow microneedle" refers to a specific microscopic structure that is designed for piercing the stratum corneum to facilitate the delivery of drugs through the skin. By way of example, microneedles can include needle or needle-like structures, as well as other structures capable of piercing the stratum corneum and delivering fluid to skin or tissue layers beneath the stratum corneum.

As used herein, "travel distance" refers to the distance traveled by an element of the delivery system upon actuation of delivery system. For example, the travel distance for a stored energy device may be different than the travel distance for the array.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a," "an," "the," "at least one," and "one or more" are used interchangeably. Thus, for example, a delivery system comprising "a" stored energy device can be interpreted to comprise "one or more" stored energy devices.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

Figure 1:
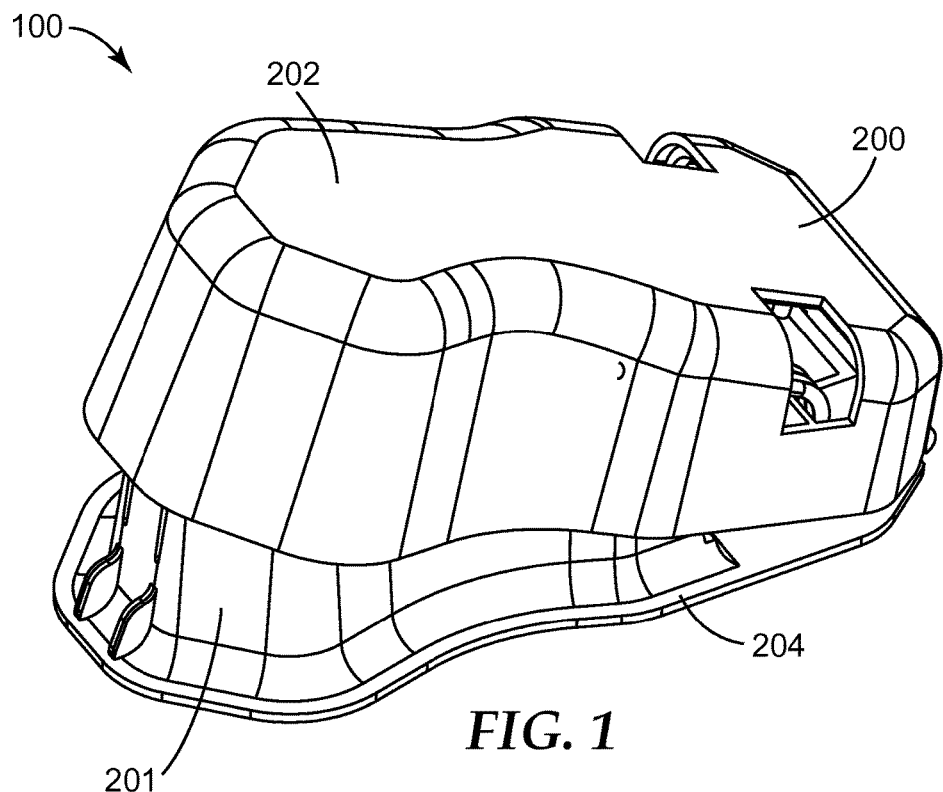
FIG. 1 is a perspective view of one exemplary embodiment of a delivery system according to the present disclosure.
Figure 2:
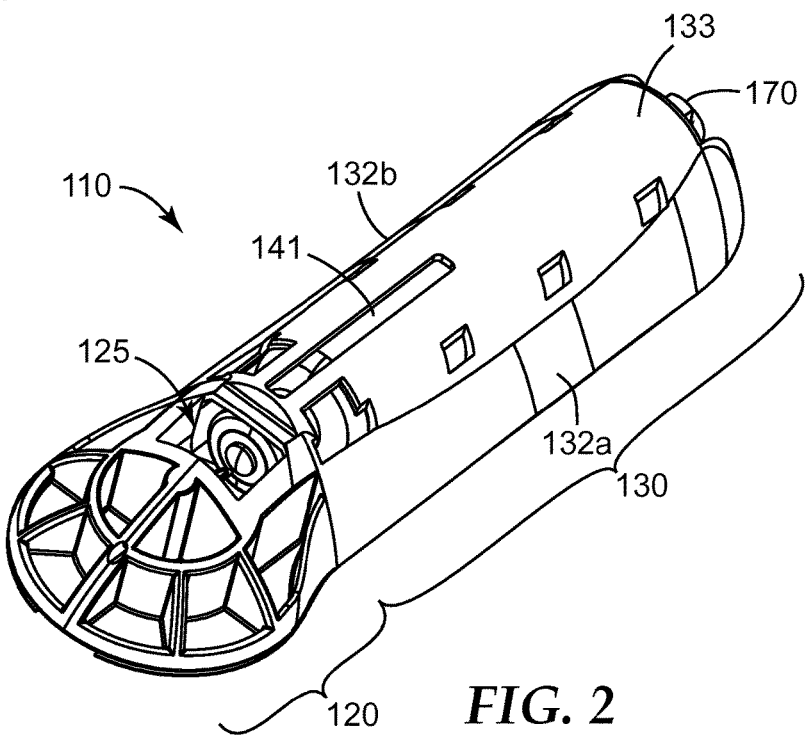
FIG. 2 is a perspective view of an infusion device according to one embodiment of the present disclosure.
Figure 3:
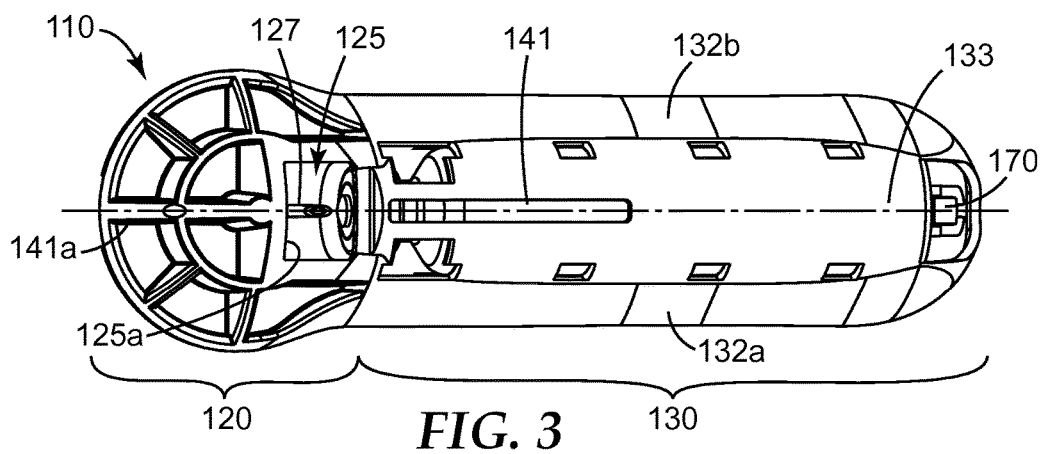
FIG. 3 is a top down view of the infusion device of FIG. 2.
Figure 4:
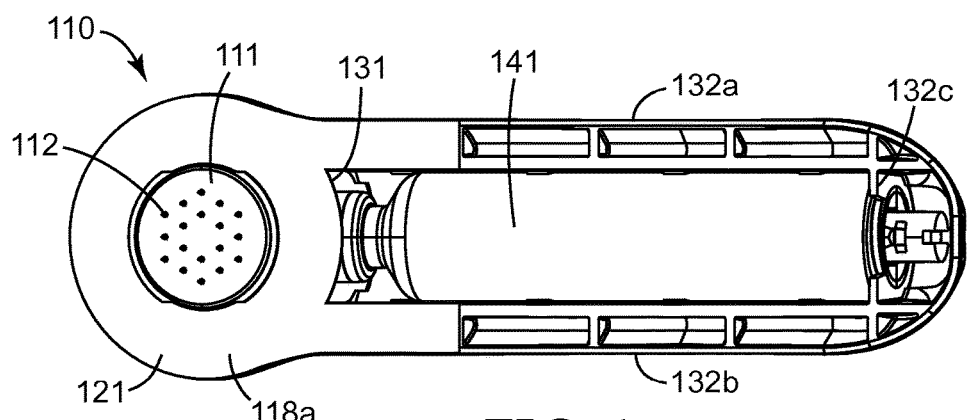
FIG. 4 is a bottom view of the infusion device of FIG. 2.

While the above-identified figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

The delivery systems of the present disclosure include embodiments that can be activated by a single actuation to reliably penetrate a patient's skin by a microneedle array, for instance a hollow microneedle array, and then release and dispense thereto a stored fluid from a reservoir (e.g., a ready-to-use drug cartridge) in a controlled manner that ensures consistent fluid delivery. Customizable and efficacious delivery of a wide variety of fluids and dosages to individual patients can be achieved in a relatively trauma free manner, while the low profile of the fluid delivery elements reduces any likelihood of the hollow microneedles becoming dislodged during penetration and encourages hands-free wear.

In certain embodiments, a single infusion device can be delivered to the skin by an applicator. The infusion device typically includes a fluid storage and delivery system, as well as a microneedle array of hollow microneedles. The fluid storage and delivery system can include a fluid reservoir, a fluid, and a mechanism for delivering the fluid from the reservoir to the microneedle array. This delivery mechanism can include a stored energy device configured to displace the reservoir, create a fluid pathway between the array and the interior of the reservoir, and force fluid from the reservoir into the fluid pathway. The infusion device can further include an adhesive proximate the array for securing the infusion device to a patient's skin. These features may be contained in a unitary housing that is low profile and easy for a patient to wear on the skin for an entire fluid delivery or extraction process.

Exemplary applicators suitable for delivering the infusion device can feature a housing defining a cavity. The infusion device can be held in the cavity by a temporary retaining mechanism that, when released, allows the infusion device to be driven toward a target surface. It may be desirable, in certain circumstances, that the infusion device is rotatable in the housing about a pivot point or hinge. Certain applicators of the present disclosure also include a stored energy device in the cavity that is actuatable to deliver the infusion device to the skin surface.

An exemplary delivery system can be provided pre-primed, in that: 1) the infusion device includes the fluid; 2) the infusion device is retained in the cavity; and 3) the stored energy device is actuatable to release its potential energy. This may be beneficial in certain circumstances, as the hollow microneedles can be protected within the housing from inadvertent destruction or contamination by a patient or other user. In other circumstances, individual components can be provided separately, with the user assembling at least some aspects of the delivery system.

In one embodiment of a delivery system according to the present disclosure depicted in FIGS. 1-9, a delivery system 100 includes an infusion device 110 and an applicator housing 200. The infusion device includes a microneedle array 111 and a fluid storage and delivery system 140. The fluid storage and delivery system 140 includes at least one reservoir 141 (which can, in some embodiments, be a drug cartridge). In certain embodiments, elements of the fluid storage and delivery system 140 can be attached to the infusion device by manufacturers, assemblers, or users. In addition, the design of certain embodiments of the infusion device 110 can enable reservoir 141 and hollow microneedles 112 to be replaced, thereby permitting reuse of the infusion device 110. In addition, the reservoirs may be more easily cleaned, sterilized, filled, and refilled as compared to microneedle devices having fixed or dedicated drug reservoirs integral therewith.

The infusion device 110 is adaptable to be "worn" by a patient during infusion/injection of fluid 142. In these exemplary embodiments, the infusion device 110 can be directly affixed to a patient's skin to accommodate either stationary or ambulatory movement during infusion, while keeping the hollow microneedles 112 inserted in the skin at an appropriate penetration depth(s).

Turning to FIGS. 2-6, an exemplary embodiment of an infusion device 110 includes a carrier head 120, an elongated reservoir housing 130, and an actuator 170 proximate the reservoir 141. The carrier head 120 includes generally planar contact surface 121. The microneedle array 111 is coupled to a least a portion of the contact surface 121, while the reservoir 141 (e.g., drug cartridge) is received in and/or contained within reservoir housing 130. As depicted, the carrier head 120 and reservoir housing 130 are integral. In other embodiments, the carrier head and reservoir housing are provided as separate components and are fastened or bonded together according to attachment means well known by those having skill in the art.

The infusion device 110 can also be provided with a base securable to and coextensive with at least a portion of the bottom surface of the reservoir housing 130. The base may prevent the fluid storage and delivery system from being inadvertently displaced or removed. The base may also be coupled to and coextensive with at least a portion of the carrier head 120 and accordingly define at least a portion of the contact surface 121.

An adhesive layer 118 can be joined to all or part(s) of contact surface 121, as well as a portion of the bottom surface 131 (or base) of the reservoir housing 130. The adhesive layer 118 (e.g., FIG. 6) may be comprised of any suitable type for the purposes described herein and may comprise, in one embodiment, a pressure sensitive adhesive covered by a release layer (not shown), the release layer could be removed prior to application of the pressure sensitive adhesive layer on the patient. Many suitable pressure sensitive adhesives can be used in adhesive layer 118, such as, but not limited to, polyacrylates, polyisobutylenes, and polysiloxanes.

The adhesive layer 118 can be located immediately adjacent the microneedle array 111. As illustrated the adhesive layer 118 includes an annular portion 118a surrounding the microneedle array 111 (e.g., FIG. 6). The annular portion 118a can have higher strength adhesive qualities than the remaining portion of adhesive layer 118 to ensure an even more secure coupling to the skin in the area surrounding needle penetration. Variations may be made to the formulations of adhesive layer 118 for varying the strength of the adhesive securing the infusion device 110 to a patient's skin as well as other bodily tissues.

Figure 5:
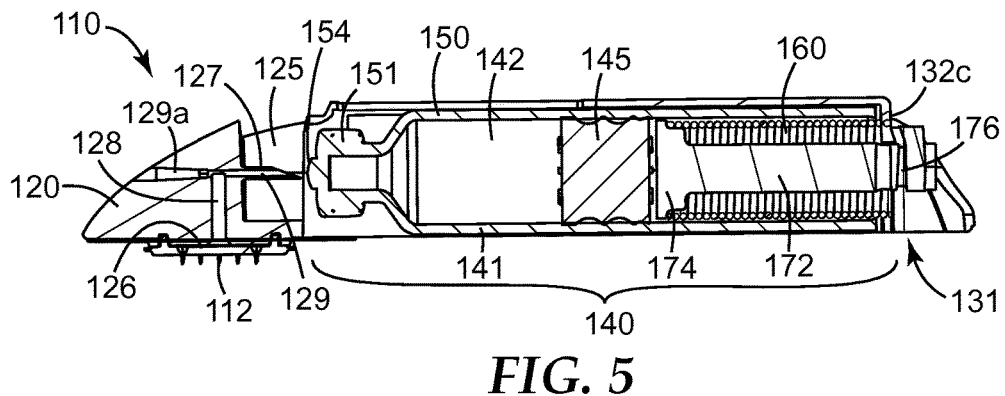
FIG. 5 is a longitudinal cross-sectional view of the infusion device of FIG. 2.

With particular reference to FIG. 5, the carrier head 120 further includes a cavity 125, at least one piercing needle 127 extending into the cavity 125, a carrier reservoir 126, and a fluid pathway 128 between the piercing needle 127 and carrier reservoir 126. The cavity 125 is configured to receive at least a portion of an openable end of the reservoir 141. As depicted, the cavity 125 is accessible via opening in the carrier head 120. In other embodiments, the cavity can be covered with a transparent or opaque material to protect the piercing needle(s) 125 therein.

The piercing needle 127 can comprise at least one cannula, manifold inlet tube, or other form of piercing needle. The piercing needle 127 establishes a fluid path that operates to fluidly connect the fluid 142 in reservoir 141 to the carrier reservoir 126 above the microneedle array 111. As such, fluid 142 may be dispensed by infusion/injection into a patient's skin through hollow microneedles 112. In one exemplary embodiment, piercing needle 127 may comprise a lumen 129 therethrough. The lumen 129 is in fluid communication with fluid pathway 128. In certain embodiments, the lumen 129 may include bore 129a through a portion of the carrier head 120. In certain embodiments, the bore 129a is sealed or otherwise plugged with stopper material e.g., a plastic or silicone rubber plug.

The piercing needle 127 is dimensioned in length to ensure the opening of a sealed but openable end 141a of reservoir 141 as will be explained below. The piercing needle 127 also has sufficient strength to accomplish this without buckling or otherwise failing. A wide variety of materials may be used for piercing needle 127. Towards this end, the materials may include, but are not limited to, metals including stainless steel, plastics, ceramics, composite materials, and combinations thereof.

As depicted in FIG. 5, the carrier reservoir 126 is disposed above the microneedle array 111 and proximate contact surface 121. In other embodiments, the carrier reservoir 126 is offset from the center of the microneedle array 111 or positioned elsewhere in the carrier head 120. In yet other embodiments, the carrier reservoir 126 is coupled to the carrier head 120 as e.g., a part of a microneedle applicator plate. In further embodiments, the carrier reservoir 126 can be created between a surface of the array and a surface of the housing. In any embodiment including a carrier reservoir, the carrier reservoir is in fluid communication with the fluid pathway at some point prior to release of the fluid in the reservoir.

Referring back to FIGS. 2-5, aspects of the reservoir housing 130 are further illustrated. The reservoir housing 130 includes a retaining wall assembly extending from a base. The retaining wall assembly includes spaced apart retaining wall portions 132a and 132b having a series of protrusions for retaining and guiding reservoir 141 along a longitudinal axis 141 a toward the cavity 125. As illustrated, retaining wall portions 132a and 132b are connected by rounded cover 133 and a posterior wall portion 132c. A fluid storage and delivery system 140 is received in the reservoir housing 130 between the retaining wall portions 132a and 132b.

Figure 6:
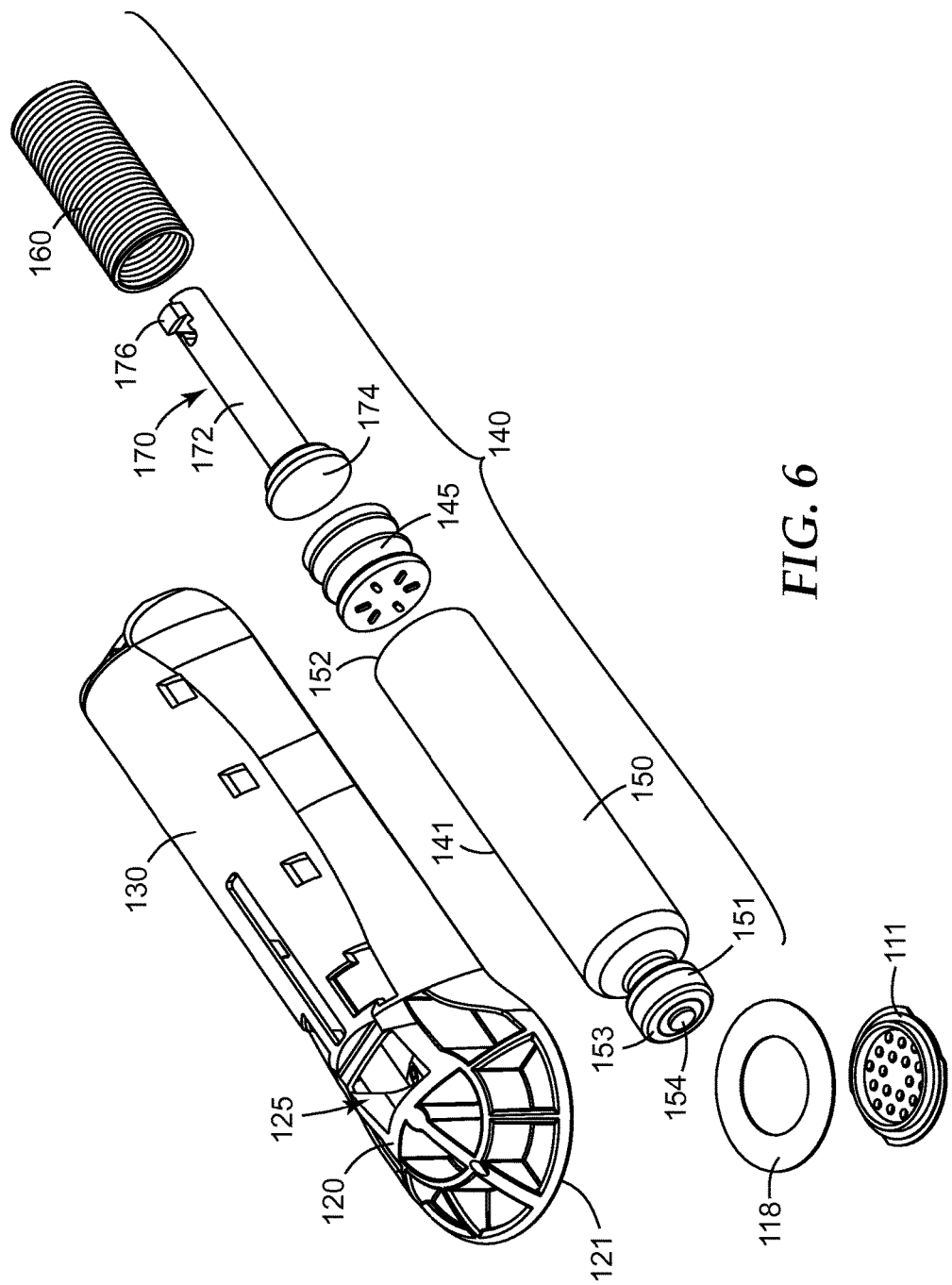
FIG. 6 is an exploded perspective view of the infusion device of FIG. 2.

Reference is now made to, for example, FIGS. 5 and 6. The fluid storage and delivery system 140 includes reservoir 141 that is cooperable with a first stored energy device 160. As will be described, first stored energy device 160 is operable to provide forces for opening an openable end of a reservoir to establish a fluid pathway to the carrier head. The stored energy devices of the present disclosure include at least one stored energy device from a group consisting of: spring devices, gaseous propellants, chemicals, motors, electrical devices, and combinations thereof.

While reservoir 141 is depicted and described as a drug cartridge, the present disclosure envisions the use of a wide variety of reservoirs having a variety of sizes and constructions that function similarly. In this exemplary embodiment, reservoir 141 may include an elongated and relatively thin walled tubular glass cylinder 150. The glass cylinder 150 may be annealed, transparent, have hydrolytic resistance to the fluids being used, and be strong enough to resist cracking or otherwise bursting when pressurized in the manner as described herein. In an illustrated exemplary embodiment, glass drug cartridges typically have enhanced lubricity on their interior wall surface, such as by using a silicone (e.g., bonded to the glass surface or coated onto the glass surface). Other materials for the reservoir drug cartridge may include, but are not limited to, polymers of various types including chlorobutyl rubber, bromobutyl rubber, silicone rubber, and polyfluorinated materials to avoid reaction to contained fluids. Polymers typically possess friction coefficients that permit piston travel within the glass cylinder.

A glass cylinder 150 includes an openable end 151 and a distal end 152. The openable end 151 is typically closed and sealed by end cap 153. The end cap 153 includes a first major surface that is arranged generally perpendicular to the major plane of the microneedle array when the reservoir is received in the reservoir housing. The end cap 153 can be secured to a neck portion of glass cylinder 150 at end 151. The end cap 153 may include a metallic cap, such as an aluminum cap, that is crimped to end 151 in a known manner. The end cap 153 may hold a septum 154 that sealingly closes an otherwise open end 151.

The septum 154 may be made of many different materials including those typically used with reservoirs (e.g., drug cartridges). The septum 154 may be made of a pierceable and resealable elastomeric seal or septum that is securely mounted, with or without being crimped, across end 151. Typically, elastomers may be crimped onto an end of a glass cylinder, with malleable material, such as aluminum. Other similar septum materials and modes of securing it to the end of the glass cylinder 150 may be used. For example, a septum molded into the body of a cylinder may be used, such as the CZ series available from West Pharmaceutical Services, Inc, Lionville, Pa., a cap, such as a standard syringe luer cap, or a molded end thin enough to be pierced. Suitable materials are subject to piercing with sufficient piercing force and maintain a seal once pierced. As noted above, septum 154 is pierced during use and preferably seals around the piercing needle with enough force to prevent leakage during pressurization and transfer of fluid 142 from the reservoir 141. Certain septum materials allow the septum to reseal following withdrawal of a needle after use. The present disclosure envisions unsealing or opening the otherwise closed septum 154 by a variety of approaches.

The reservoir 141 includes a piston 145 that is in a sliding and sealing relationship with respect to interior walls of glass cylinder 150. This provides adequate sealing for a fluid storable in an interior variable volume chamber formed between piston 145 and openable end 151. Given the volume variability of this interior chamber, the glass cylinder can be configured to accommodate any intended dosage volume.

Such a reservoir 141 (e.g., a drug cartridge) may be of the type wherein pre-filled drugs are ready-to-be used, such as the fluids noted below. The glass cylinder 150 may be of the kind that satisfies standards, including international standards, such as the International Organization for Standards (ISO). In addition, glass cylinder 150 can be relatively easy to clean and sterilize.

The present disclosure also contemplates the use of valve mechanisms for opening an openable end of a drug cartridge or a reservoir for allowing transferring of a fluid to the hollow microneedles 112. For example, a valve member retained in a reservoir similar to the drug cartridge may be opened from a fluid blocking or closed condition by having it cooperate with structure (not shown), for example a cannula, on the carrier head/within the cavity, as the two are brought into operative engagement. Suitable valve mechanisms include, but are not limited to, those disclosed in International Publication No. WO2005/018705 to Cindrich et al.

Referring back to the piston 145, it is adapted to travel along a length of reservoir 141 until fluid 142 is completely (or nearly completely) forced or expressed therefrom. Typically, piston 145 may be made of materials that seal against the body of reservoir 141, but are also inert with respect to the fluid. For example, purified elastomeric materials such as halobutyl rubber and silicone rubber materials may be typically used for such pistons, but other materials such as non-elastomeric materials are also contemplated. In addition, piston 145 can be made of diverse materials including laminated constructions. While the illustrated embodiment uses one kind of piston, others can be utilized, including those contoured to substantially match the interior shape of the openable end 151.

Other means to reduce void space in the cartridge are contemplated. For example, small spherical objects can be included in the reservoir 141. When the piston 145 moves forward and pushes the fluid out of the cartridge, the small spherical objects are also pushed forward into the neck of the cartridge and around the piercing needle. The spherical objects are preferably larger than the fluid pathway in the piercing needle so as avoid plugging the fluid pathway. Instead, the spherical objects preferably pack around the piercing needle and displace fluid in the cartridge neck space. The spherical objects can be made of metal, plastic, glass, ceramic, or other material that is compatible with the fluid in the reservoir.

The reservoir 141 has longitudinal axis 141a that is, in one exemplary embodiment, generally parallel to a patient's skin when coupled to or adhered to the skin surface. In other embodiments, the reservoir 141 is disposed at non-zero angles relative to the skin. In embodiments wherein a low profile for the infusion device is desired, the longitudinal axis 141a is generally parallel to the major plane of the microneedle array 111. The reservoir 141 can be a transparent glass drug cartridge to enable visual observations relating to the progress of fluid dispensing. This can be advantageous particularly in infusion situations that may take relatively long periods. Such a glass drug cartridge may be of a commercially available type, such as from Schott North America, Elmsford, N.J., USA, and West Pharmaceutical Services, Inc. of Lionsville, Pa., USA. Other kinds of reservoirs having similar properties are well within the scope of the disclosure.

When made of glass, the reservoir 141 may also be advantageous in regard to enhancing the versatility of the delivery systems of the present disclosure. One potential advantage is that reservoirs 141 can conform to the sizes and shapes already familiar in the pharmaceutical field and are readily fillable using commercial equipment. In addition, because reservoir 141 may be packaged separately from the infusion device 110, users may be able to use custom reservoirs and easily install them in the infusion device 110 at the point of use. Moreover, by being able to use known drug cartridges, patients are able to use a wide variety of drugs and dosages dispensed in a manner particularly tailored to them and not be dependent on a manufacturer of the dispensers having fixed reservoirs.

A typical glass drug cartridge reservoir 141 may have dimensions that range from 2 cm to about 8 cm in terms of their length, and may have inner diameters that range from 4 mm to 12 mm. More typically, the lengths may range from 4 cm to 6 cm, and the inner diameters from 6 mm to 10 mm. The present disclosure contemplates other dimensions depending on, for example, the size of the drug dispensing cartridges. While a transparent glass drug cartridge reservoir 141 may be used, other materials may also be used. These materials and construction are preferably compatible to the fluids contained and able to withstand the pressures generated during use.

Turning now to FIGS. 5-6, aspects of an exemplary stored energy device will be described. In the illustrated embodiment, an actuator, depicted as spring release 170, is operable to release the first stored energy device 160. In one exemplary embodiment, first stored energy device 160 includes an elongated coil spring. The spring release 170 may include a latch 172 that is attached at one end to a plunger 174 abutting the piston 145. The first stored energy device 160 is disposed between plunger 174 and rear wall portion 132c to be loaded in a manner that provides sufficient operating forces for displacing reservoir 141 when the first stored energy device 160 is released by spring release 170.

In certain embodiments, the latch 172 and the plunger 174 may be separate from each other. In other embodiments, however, they can be coupled. They may be made of similar or dissimilar materials, such as suitable plastics and metal. The latch 172 can be elongated as illustrated or may have a shorter length. A longer length can facilitate removal of first stored energy device 160 from reservoir 141. A projection 176 of latch 172 is coupled to rear wall portion 132c of reservoir housing 130, thereby retaining first stored energy device 160 in a latched and loaded condition. While the projection 176 on latch 172 is illustrated for cooperating with the retaining wall, and acting as the user-engageable portion of an actuator, the present description envisions other spring release mechanisms known to those having skill in the art.

To release the first stored energy device 160, a user pushes the latch 172 downward to disengage the projection 176 from the rear wall portion 132c. The first stored energy device 160 then displaces reservoir 141 axially along the longitudinal axis 141a until the openable end 151 reaches cavity wall portion 125a on the carrier head 120. As the reservoir 141 is driven into the cavity 125 by the first stored energy device 160, the openable end 151 engages the piercing needle 127. The projection 176, or other release mechanism, thus essentially acts as the user-engageable portion of an actuator, allowing release of the potential energy in the stored energy device to commence fluid delivery.

In an alternative embodiment, the first stored energy device 160 includes of a pair of spring devices. The first spring device may be a coil spring suitably interposed between posterior retaining wall 132c and the reservoir 141 to displace the latter in the direction of the carrier head 120 upon activation. A second spring device can be another coil spring for forcing piston 145 to expel or force fluid into fluid pathway 128. Additional combinations and configurations of stored energy devices to displace both the reservoir and the piston can be found in International Publication No. WO2011/014514 (Gonzalez et al.), and can include Belleville washers, gaseous propellants, multi-diameter springs, and bifurcating springs. Particularly suitable bifurcating springs may be found in International Publication No. WO2013/055638.

As the openable end 151 of the reservoir 141 is driven into cavity 125, the piercing needle 127 pierces septum 154 and eventually establishes a fluid passage between the reservoir 141 and the carrier head 120 for communicating fluid therebetween. The first stored energy device 160, via plunger 174, urges piston 145 forward to compress the chamber and force fluid 142 through the now opened septum 154 into lumen 129. From the piercing needle 127, the fluid flows through the fluid pathway 128 and the carrier reservoir 126 into the hollow microneedles 112. Because the rate of reservoir and plunger displacement (and thus fluid delivery) are at least partially controlled by a stored energy device, the forces acting on the system can be controlled generally regardless of user-applied forces. This is advantageous over other systems that require manual pushing and/or sliding of a member in order to affect a release and dispensing of fluids. Excess manual pushing or pulling forces can cause the hollow microneedles to dislodge, thereby defeating the intended results of the apparatus.

It is further contemplated that the infusion device be used to extract fluid (e.g., interstitial fluid) from the dermis. As can be appreciated, a reservoir can be provided with a piston proximate the openable end, leaving little to no fluid volume. In such embodiments, the first stored energy device comprises two components. The first component is operable to drive the reservoir in the direction of the piercing needle. The second component is operable to move piston in the opposite direction, thereby causing fluid to flow from target tissue toward the reservoir.

To replace used drug cartridges, a user may pull on latch 172 with a suitable hand tool (not shown) to recompress the first stored energy device 160. As such, a user can separate the piercing needle and the septum. Consequently, the reservoir 141 and the latch 172 may be removed and potentially replaced. Thus, a user need only replace a reservoir instead of using a new device. Furthermore, the first stored energy device 160 can be reused as well as the latch 172 and plunger 174. Typically, however, the microneedle array 111 is also replaced.

Consequently, the manufacturer or optionally the user may easily install a ready-to-use reservoir 141. This can be accomplished by, e.g., inserting a drug cartridge and subsequently inserting a stored energy device in their illustrated positions in reservoir housing. Allowing the reservoir 141 and first stored energy device 160 to be installed separately is another method to pressurize the fluid at the point of use and avoid pressurization of the fluid during storage, As described above, the infusion device 110 includes a microneedle array 111 coupled to the contact surface 121 of the carrier head 120 for penetrating a patient's skin surface with microneedles 112. The microneedle array 111 can be permanently coupled or removably coupled to a surface of the carrier head 120. In another embodiment, microneedle array 111 may include a microneedle applicator plate coupled to the contact surface 121, which includes an array of hollow microneedles 112 formed therein and protruding therefrom. As noted above, the microneedle array or microneedle applicator plate may at least partially define or include a volume above the hollow microneedles that can act as the carrier reservoir 126.

The microneedle array 111 can be connected, for example, by ultrasonically welding it to the carrier head 120. The present disclosure also envisions holding a microneedle array or microneedle applicator plate to the carrier head 120 by a variety of techniques including, but not limited to, snap-fits, adhesives, such as a UV curable, heat curable, or two-part bonding agent, spin welding, and other similar approaches. While fixed connections are described, releasable connections may be provided, such as in situations involving reusing the infusion device, whereby used microneedles (with or without an applicator plate) may be replaced. Suitable releasable couplings include pressure-sensitive adhesives and the like.

The hollow microneedles 112 typically can have a length of greater than 100 μm to about 3 mm. In other embodiments, hollow microneedles 112 may have a length that ranges from 250 μm to 1500 mm, more typically, a length of from 700 μm to 1300 μm. In some embodiments, hollow microneedles 112 may penetrate into the skin of a patient to a depth of from 150 μm to 1500 μm. More typically, they penetrate into the skin to a depth of from 500 μm to 1000 μm, more typically from 600 μm to 900 μm. It will be appreciated that the depth of penetration of the hollow microneedles 112 may not be the full length of the hollow microneedles themselves.

The hollow microneedles 112 can be arranged in the microneedle array 111 to have a spacing of about no less than 0.7 mm on average between adjacent hollow microneedles. More typically, the microneedle array 111 may have the hollow microneedles 112 spaced an average of at least 2 mm apart from each other. The hollow microneedles 111 can have an average channel bore (not shown) of 10 to 3000 μm$^2$ cross-sectional area, more typically, the average channel bore may range from 700 to 2000 μm$^2$. The hollow microneedles 112 on array 111 may have a spacing density of 3 to 18 microneedles per cm$^2$. The bores (not shown) may allow a fluid to be dispensed at rates of at least 20 μL/min and no greater than 500 μL/min. The bore may terminate in an exit hole or port located on a sidewall of each hollow microneedle, or a sidewall portion that is adjacent the needle tip.

The present disclosure contemplates all forms of microneedles that can deliver fluid. Also, it will be understood that the foregoing values are illustrative and not necessarily limiting. It will be further understood that the present disclosure envisions the use of other needle assemblies for injection and infusion (or extraction) besides hollow microneedles. As such, the needle lengths may be longer than noted above. Also, the depth of penetration of hollow microneedles 111 may vary from needle to needle. The hollow microneedles typically enable penetration into the dermis of a patient in a manner that minimizes or reduces trauma, e.g., erythema and pain. It will be understood that a relationship of trauma and various infusion/injection parameters exist, such as is described in commonly-assigned U.S. Patent Publication No. 2011/0213335 to Burton et al.

Any substance that can be formulated in a fluid and delivered via hypodermic injection may be used, including any pharmaceutical, nutraceutical, cosmeceutical, diagnostic, and therapeutic agents (collectively referred to herein as "drug" for convenience). Examples of drugs that may be useful with the present invention include but are not limited to ACTH (e.g., corticotropin injection), luteinizing hormone-releasing hormone (e.g., Gonadorelin Hydrochloride), growth hormone-releasing hormone (e.g., Sermorelin Acetate), cholecystokinin (Sincalide), parathyroid hormone and fragments thereof (e.g., Teriparatide Acetate), thyroid releasing hormone and analogs thereof (e.g., protirelin), secretin and the like, Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as Hirulog, IgE suppressors, Insulin, insulinotropin and analogs, Insulin-like growth factors, Interferons, Interleukins, Luteinizing hormone, Luteinizing hormone releasing hormone and analogs, Heparins, Low molecular weight heparins and other natural, modified, or synthetic glycoaminoglycans, M-CSF, metoclopramide, Midazolam, Monoclonal antibodies, Peglyated antibodies, Pegylated proteins or any proteins modified with hydrophilic or hydrophobic polymers or additional functional groups, Fusion proteins, Single chain antibody fragments or the same with any combination of attached proteins, macromolecules, or additional functional groups thereof, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne Japanese encephalitis, pneumococcus, streptococcus, typhoid, influenza, hepatitis, including hepatitis A, B, C and E, otitis media, rabies, polio, HIV, parainfluenza, rotavirus, Epstein Barr Virsu, CMV, chlamydia, non-typeable haemophilus, moraxella catarrhalis, human papilloma virus, tuberculosis including BCG, gonorrhoea, asthma, atherosclerosis malaria, *E. coli*, Alzheimer's Disease, *H. Pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, and sexual hypofunction and tranquilizers. The present description envisions that even a gaseous fluid may be utilized.

Figure 7:
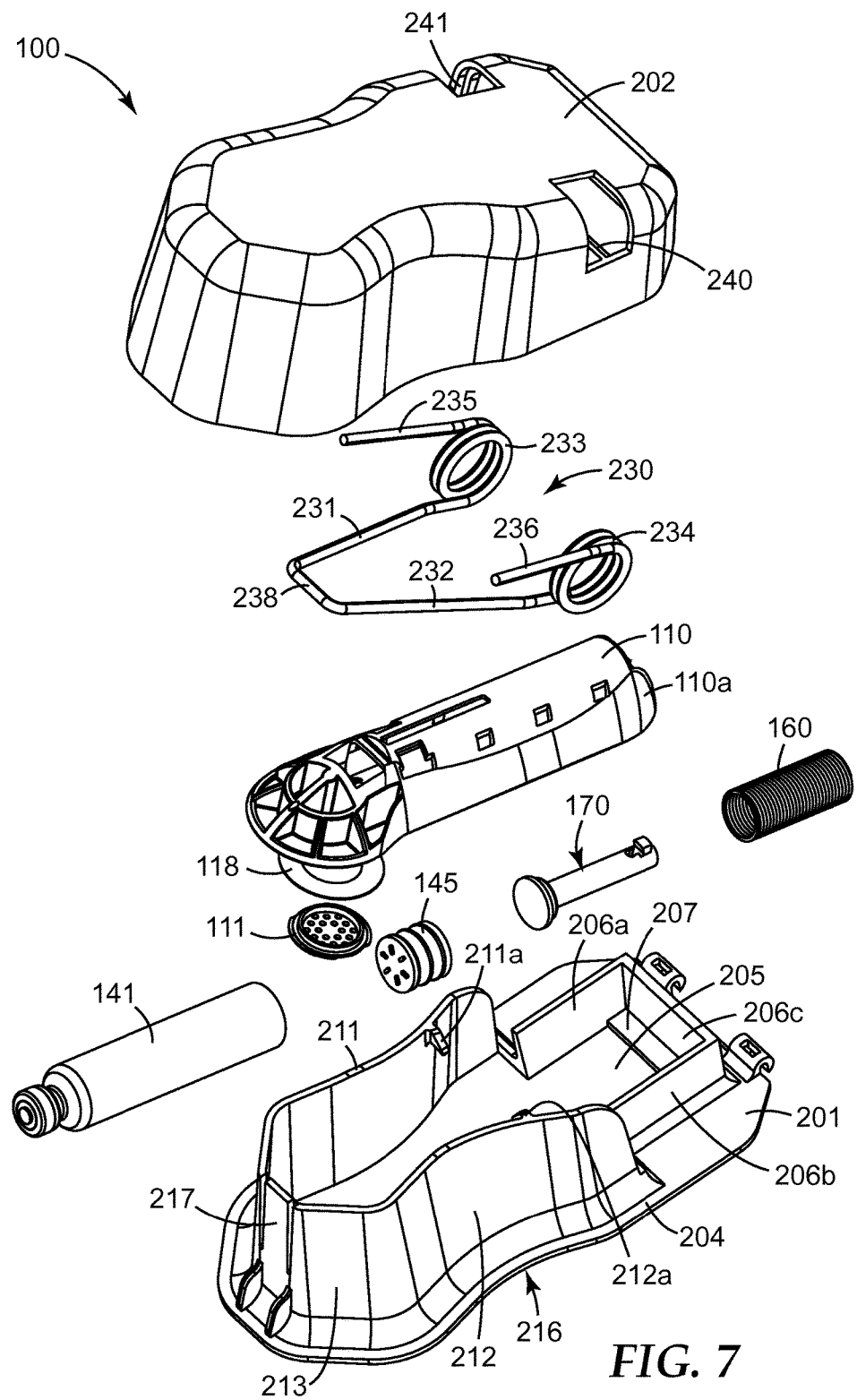
FIG. 7 is an exploded perspective view of the applicator housing illustrated in FIG. 1.
Figure 8:
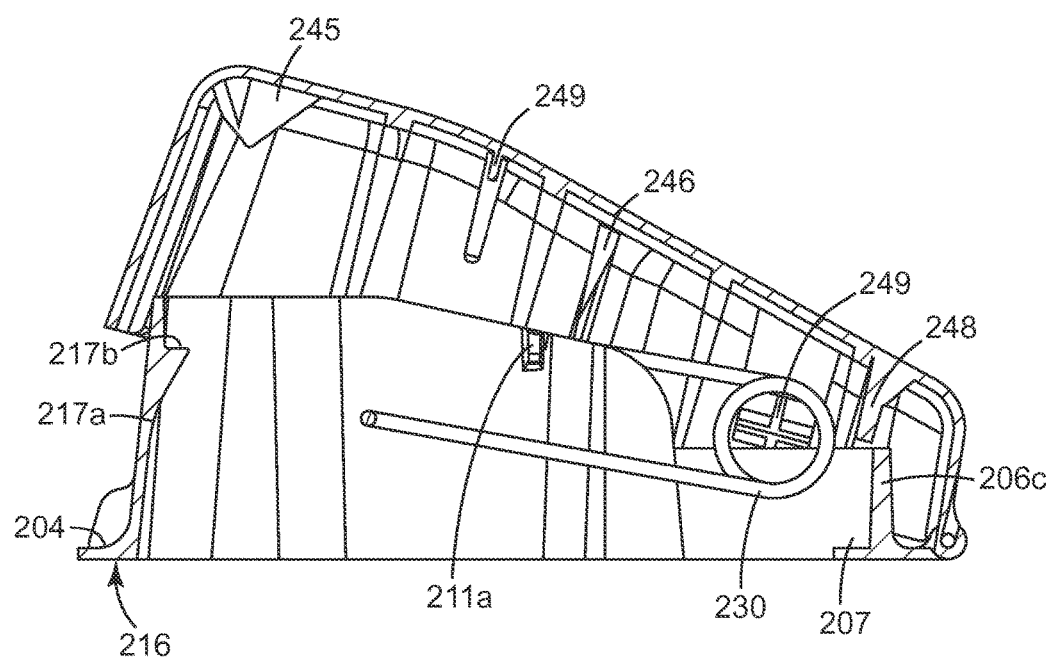
FIG. 8 is a longitudinal cross-sectional view of the delivery system in FIG. 1.
Figure 9A:
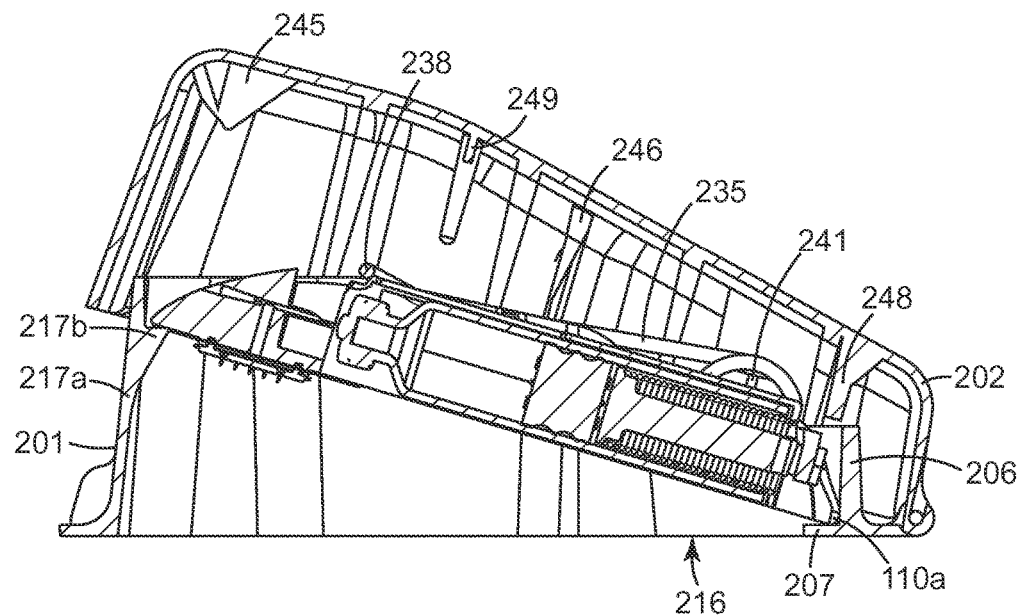
FIG. 9A is a longitudinal cross-sectional view of the delivery system of FIG. 1 in a pre-primed configuration.
Figure 9B:
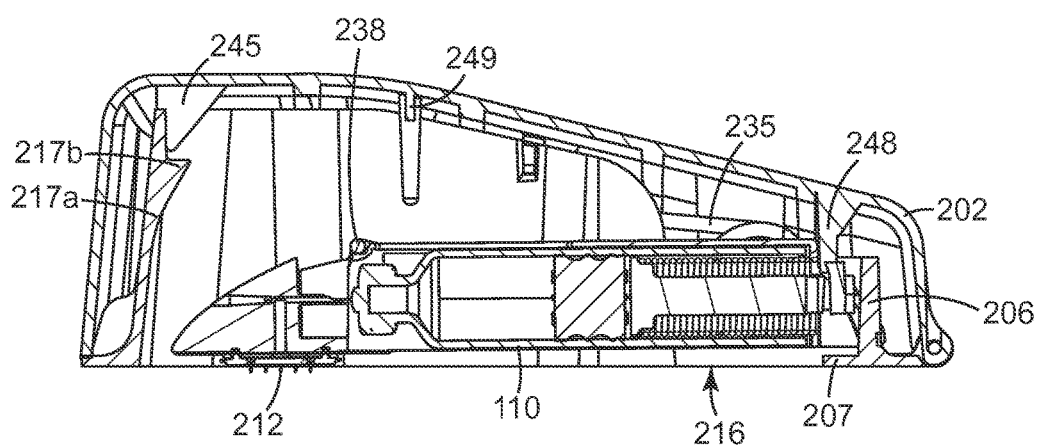
FIG. 9B is a longitudinal cross-sectional view of the delivery system of FIG. 1 after actuation.

One embodiment of an applicator housing 200 for delivering infusion device 110 to a patient's skin is depicted in FIGS. 7-9. The housing 200 may be self-contained and compactly constructed to provide a relatively low profile and small footprint for, among other factors, ease of use and patient comfort. In the illustrated embodiment of FIGS. 8 and 9, housing 200 may include a lower housing portion 201 and mating upper housing portion 202 that provides a cover. The lower and upper housing portions 201 and 202 may be secured together by any suitable means including, but not limited to, snap-fit together or coupled by hinges, pivots, frictional interference fits, fasteners, and the like. In certain preferred embodiments, the lower and upper housing portions 201 and 202 are connected together by a hinge (not shown) that allows clamshell-like pivoting of the upper housing relative to the lower housing. The materials of housing 200 may include, but are not limited to, plastics, metals, composite materials, and combinations thereof. In certain embodiments, plastics capable of being thermoformed are preferred.

The lower housing portion 201 may include a base 204, which may be generally planar, defining an opening 205 for allowing infusion device to contact a patient's skin surface. In certain embodiments, the opening 205 may be shaped to the profile of the infusion device 110. As can be appreciated, the first major surface 216 of the base member 204 will typically be proximate a patient's skin when the infusion device 110 is delivered.

The lower housing portion 201 can further include mechanisms for releasably securing the infusion device 110 within the applicator housing 200. Sidewall portions 211 and 212 extend from the base 204 and can be connected by rounded portion 213. The rounded portion 213 can include a releasable retaining mechanism 217 spaced from the base 204. In the illustrated embodiment, the releasable retaining mechanism 217 includes a ledge 217a and a tab portion 217b. The tab portion 217b is movable relative to the rounded wall portion 213 and can be coupled to or integrally formed therewith. A portion of the carrier head 120, typically contact surface 121, can rest on the ledge portion 217b. As will be explained in further detail below, user-prompted movement of the tab portion 217a displaces the ledge 217b, which releases the infusion device 110 resting thereon.

It is further contemplated that infusion device 110 be releasably secured in the housing 200 by different means. For example, the sidewall portions 211 and 212 can include projections or other protrusions that engage a portion of the carrier head 120 or the reservoir housing 130. Such protrusions can initially retain the infusion device 110 at an angle relative to first major surface 216 and thereafter provide negligible interference when a user applies an actuation force, as described below. Similarly, the rounded portion 213 may include a fixed nub or other protrusion that initially retains the carrier head 120. In other embodiments, the infusion device can be releasably coupled to a portion of the upper housing 202 via releasable adhesive, clasp, latch, magnet, or other temporary attachment means known to those having skill in the art.

The lower housing 201 can further include a holding chamber for the distal end 110a of the infusion device 110. In the illustrated embodiment, the holding chamber includes a pair of spaced apart walls sections 206a, 206b, a rear wall section 206c, and a shelf 207 that is generally parallel with the first major surface of the base. In certain embodiments, the chamber wall sections 206a, 206b are spaced apart by a dimension approximating the width of the reservoir housing 130 at the distal end 110a, thereby reducing side-to-side movement of the infusion device 110 within the housing.

The distal end 110a of the infusion device 110 is received near or against the rear wall section 206c and rests upon the shelf 207. When the delivery system is primed for use, as will be explained below, the carrier head 120 of the infusion device 110 is moved towards the upper housing 202, while the distal end 110a is retained in the holding chamber proximate the base. Retaining the distal end 110a proximate the base (which will be proximate the patient's skin) may allow the infusion device 110 to rotate about the distal end 110a when e.g., a stored energy device 230 is activated. Without wishing to be bound by theory, rotation of the infusion device 110 within the housing about a pivot point reduces the force needed to accelerate carrier head 120 to impact velocity and may reduce variability in velocity at skin impact. Furthermore, the pivot may increase the likelihood that the hollow microneedles 112 reach the skin at an angle substantially normal to the skin surface.

The delivery system 200 further includes a second stored energy device 230 that is actuatable for applying force to a portion of the infusion device 110 in a direction generally normal to the first major surface 216. Typically, users pushing down on microneedle dispensing devices (not shown) may use too much force or too little force, thereby resulting in unwanted variations in penetration force and depth. In some aspects, the presently described delivery system overcomes this shortcoming of other devices. In some embodiments, the actuated force allows for movement of an infusion device in a controlled manner, thereby ensuring application of the necessary forces for hollow microneedles 112 coupled thereto to penetrate the skin of a patient.

In one embodiment, the second stored energy device 230 may be a spring arranged to apply to infusion device 110 a controlled force, ensuring a consistent penetration to a targeted depth range. In the exemplary embodiment, second stored energy device 230 may be comprised of a generally U-shaped double-torsion spring. The bight portion 238 of second stored energy device 230 rests on or proximate to the carrier head 120. In other embodiments, the bight portion 238 is coupled to the carrier head or other portion of the infusion device 110. It may be preferred, however, that the force released by the stored energy device 230 be applied to the carrier head 120, ensuring acceleration of hollow microneedles 112 at the desired impact velocity. In certain embodiments, the carrier head 120 may include a groove (not shown) to receive the bight portion 238.

As illustrated in FIG. 7, second stored energy device 230 may include first leg portions 231, 232 that are disposed in the housing 200 between spaced apart retaining walls 211 and 212. The illustrated second stored energy device 230 further includes torsion coils 233 and 234, which extend to second leg portions 235 and 236. The torsion coils 233 and 234 are adapted to fit around engaging arms 240 and 241 (described below), which couples the torsion spring to the housing. The second leg portions 235, 236 are typically disposed at a location exterior to the sidewall portions 211, 212 of the lower housing 201. In the illustrated embodiment, the sidewall portions each include angled ridge members 211a and 212a that engage the leg portions 231, 232. The ridge portions 211a, 212a hold the delivery system in a closed configuration during application by limiting the upward movement of leg portions 231, 232.

In certain embodiments wherein the second stored energy device is a spring, the second stored energy device 230 is not fixed or releasably coupled to the infusion device 110. As such, following impact, the second stored energy device 230 may freely recoil upwardly and vibrate without partially or totally withdrawing or lifting hollow microneedles 112 from the skin and their intended penetration depths. As such, the potential for leakage of the fluid to the surface of the skin occurring may be reduced, minimized or even eliminated.

It will be appreciated that the magnitude and frequency of spring recoil and vibration is directly related to primary factors such as the spring's free length, mass and material properties, and any tension or preload. Other factors may include the spring's shape and configuration, such as a multi-element stacked leaf-like spring, as in a stacked flat leaf spring arrangement; single straight length as in a single piece of round spring tempered wire; shaped wire-formed U-shaped, etc. Furthermore, the second stored energy device 230 may be made with any cross-section, including, but not limited to, round, square, rectangular, any regular polygon, irregular in shape or even varying along its length. Such shape profiles may thereby confer stiffness and rigidity at portions where needed.

Materials suitable for use in the second stored energy device include a carbon steel (e.g., music wire), oil tempered based alloys (e.g., beryllium copper, phosphor bronze), or other suitable alloys (e.g., Elgiloy™ cobalt alloy commercially available from Elgin Specialty Metals, Elgin, Ill., USA). While in the present exemplary embodiment, a metallic spring may be used that has a relatively high spring energy constant for sake of compactness, it is also possible that a less compact, non-metallic (e.g., plastic) spring element may be utilized, such as where the spring element is primed and fired within a short time frame.

The second stored energy device 230 is actuatable for applying force to the infusion device, typically at a velocity before impact ranging from between about 2 and about 20 m/sec before the infusion device 110 impacts a patient's skin. More typically, hollow microneedles 112 on the infusion device 110 strike a patient's skin at a velocity before impact ranging from between about 4 and about 12 m/sec.

The upper housing portion 202 can have a construction to envelop and cooperate with the lower housing portion 201. The upper housing portion 202 can be made of a single-piece, shell-like construction that is sized and shaped to generally match lower housing portion 201 for mating therewith. In the illustrated exemplary embodiment, upper housing portion 202 may also be made of a plastic, such as polycarbonate, acrylic and other similar materials. In certain embodiments, the upper housing portion is thermoformed from, e.g., polystyrene, PVC, ABS, acrylic, PETG, polycarbonate, polyethylene, polypropylene, TPR, and TPO. The upper housing portion 202 can also be transparent to allow a user to visually inspect the delivery of the infusion device 110. Alternatively, upper housing portion 202 may have a window (not shown) that similarly allows a user to easily visually observe the infusion device 110 delivery.

The upper housing portion 202 further includes a pair of coil engaging arms 240, 241, a pair of opposing projections 243, 244, and tab engagement teeth 245. The torsion coils 233 and 234 are coupled to the engaging arms 240, 241 on opposing sides of the upper housing 202. The second leg portions 235, 236 engage the underside of the projections 246, 247. In the illustrated embodiment, the tab engagement teeth 245 are operable to displace the releasable retaining mechanism 217. Though teeth-like structures are depicted, other structures are capable of displacing the releasable retaining mechanism 217. Furthermore, in embodiments featuring a non-displaceable retaining mechanism 217 (e.g., adhesive), the engagement teeth or similar structure may not be necessary.

The present disclosure envisions that the infusion device 110 be loaded in the applicator housing before being shipped from a manufacturer or assembler of the delivery system. When the infusion device 110 is to be placed into position (i.e., loaded), it will be displaced (e.g., pulled or pushed) until the carrier head 120 engages tab portion 217b, which moves ledge 217b out of the way until it may rebound underneath the contact surface 121, thereby retaining the infusion device 110 in its primed condition. In embodiments wherein the upper and lower housing portions are connected by a hinge, the loading of the infusion device can have the effect of forcing the upper housing to rest at an non-zero angle relative to the lower housing. It will be understood that the infusion device 110 need not be stored or shipped in a loaded condition within the applicator housing, but may be shipped in a non-primed condition.

The force applied to load the infusion device 110 may also be used to displace the second stored energy device 230 and vice versa. When engaged with the carrier head 120, the bight portion 238 of the second stored energy device 230 will be driven toward the upper housing together with the first leg portions 231, 232 until the infusion device 110 engages the releasable retaining mechanism 217. Like the infusion device 110, the second stored energy device 230 can be provided to the user in a loaded or unloaded configuration.

To release the infusion device 110, a portion of the upper housing 202 is depressed downwardly. As a result, force is applied via ridges 246, 247 to the second leg portions 234, 235 of the stored energy device 230, thereby storing additional potential energy in the system by further increasing the tension in the torsion coils 233, 234. Additional and/or continued downward pressure drives the tab engagement teeth 245 toward the tab portion 217a, eventually displacing some of the tab portion 217a in a direction away from the carrier head 120. Displacement of the tab portion 217a eventually removes the ridge 217b from underneath the infusion device 110. This frees the second stored energy device 230 to drive or force the infusion device 110 downwardly, generally along a vertical axis, so that hollow microneedles 112 can penetrate the skin. In certain embodiments, the user experiences the unloading of the applicator housing in two distinct stages: 1) the initial transfer of energy to second leg portions and 2) the decoupling of the infusion device from the releasable retaining mechanism.

It is further contemplated that the force used to trigger the second stored energy device may also actuate the first stored energy device in the infusion device 110, such that the septum of the reservoir may be pierced soon after the microneedles penetrate the skin. For example, the upper housing may include a protrusion 248 configured to engage the actuator 170 as the upper housing is pressed toward the skin surface. In certain embodiments, the protrusion 248 can be configured to trigger the first stored energy device as the hollow microneedles 112 begin to penetrate the skin surface. In other embodiments, the protrusion can be designed to trigger the first stored energy device 160 prior to penetration. Myriad additional ways of triggering both stored energy devices simultaneously, near simultaneously, or sequentially will be appreciated by those having skill in the art.

The upper housing can further include shoulders 249 to prevent complete displacement of the reservoir 141 before the hollow microneedles 112 penetrate the target surface. The shoulders 249 may engage e.g., through-holes in the infusion device as the housing is closed and eventually reside proximate the openable end 151 of the reservoir 141. The shoulders 249 are capable of preventing the inadvertent displacement of the reservoir (and subsequent piercing of the septum) before the housing is separated from the infusion device. The shoulders may be beneficial if the first stored energy device is to be triggered prior to microneedle penetration.

Figure 10:
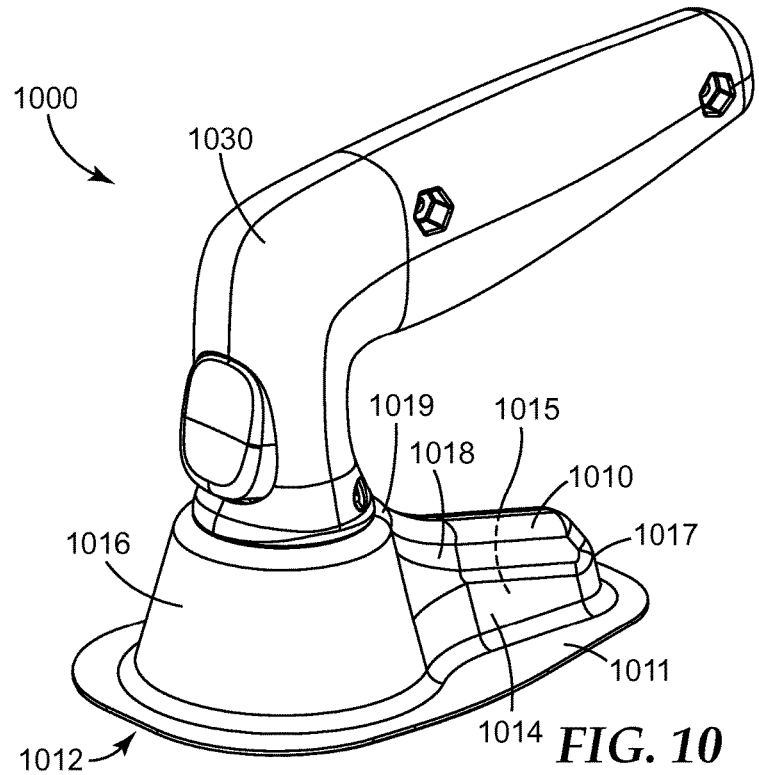
FIG. 10 is a perspective view of a delivery system according to another embodiment of the present disclosure.
Figure 11:
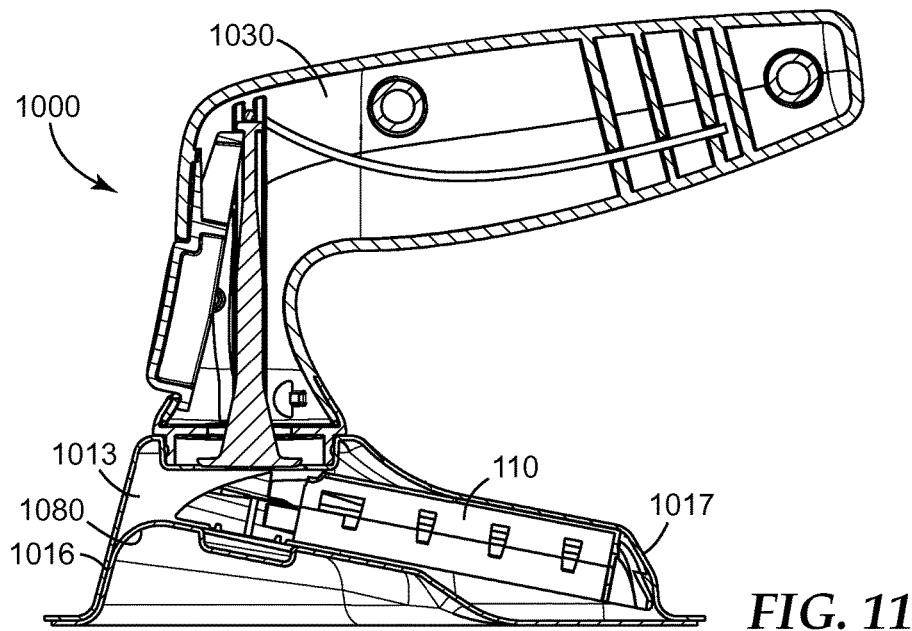
FIG. 11 is a longitudinal cross-sectional view of the delivery system of FIG. 10.

Another embodiment of a delivery system for infusion device 110 is illustrated in FIGS. 10 and 11. The delivery system 1000 includes a single housing 1010. The housing includes a base 1011 that defines an opening 1012 into an interior chamber 1013. The interior chamber 1013 is defined by sidewall portions 1014 and 1015, anterior wall 1016, rear wall 1017, and cover 1018. The cover 1018 includes an aperture 1019 sized and shaped to receive the distal end of an external applicator 1030. In certain embodiments, the aperture 1019 is designed to matingly receive the distal end of the external applicator 1030. In other embodiments, the aperture 1019 is larger than the applicator 1030, allowing the distal end to access the interior chamber 1013.

The chamber 1013 includes at least one releasable retaining mechanism (not shown) for retaining the carrier head 120 of an infusion device 110 proximate the aperture 1019. In certain embodiments, the infusion device 1020 is retained in the chamber at a non-zero angle relative to the base, such that it can rotate about its distal end 110a upon actuation. As above, the distal end 110a of the infusion device 110 can be retained against a shelf or similar structure within the housing or be allowed to pivot against the patient's skin when the delivery system is secured thereto.

The external applicator 1030 is operable to displace the infusion device 110 from proximate the aperture and toward a delivery site. Suitable external applicators include, but are not limited, those described in US Patent Publication No. 2008/0039805 to Fredrikson et al. To deliver the infusion device primed within the chamber, a user primes the external applicator by, e.g., pushing a piston into the interior of the applicator until it locks into place. The external applicator is then coupled to or received in aperture 1019. A user places the housing 1010 against the skin or other target tissue and actuates the external applicator, delivering a displacement energy to the infusion device 110. This transfer of energy drives the carrier head, including the microneedle array, towards the skin surface.

The delivery system 1000 can also be provided with a protective base 1080. As depicted in FIG. 11, the base 1080 may be at least partially received in the chamber 1013 of the housing and can, in certain circumstances, retain the infusion device 110 proximate a releasable retaining mechanism. The base 1080 is removed from the chamber prior to application to the skin or target tissue. In certain embodiments, the protective base 1080 can be integral with a substrate having a plurality of protective bases protruding therefrom. In such embodiments, multiple delivery systems may be coupled to the plurality of protective bases for delivery to a practitioner or a user.

It will be further understood that provisions are made for a method of treating a patient by infusing a fluid using a delivery system of the present invention.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A system for delivering a microneedle array to a patient's skin surface, the system comprising:
   a delivery apparatus comprising a housing comprising an upper housing pivotably attached to a lower housing; and
   an infusion device detachably received in the housing, the infusion device including;
      a reservoir having a fluid therein and an openable end including a first major surface,
      a fluid pathway proximate the openable end,
      a first stored energy device proximate the reservoir actuatable to apply energy in a direction perpendicular to the first major surface, and
      an attachment surface and an array of hollow microneedles coupled to a portion of the attachment surface, wherein the pathway is in fluid communication with the hollow microneedles
   wherein the housing is configured to provide for the infusion device replacement.

2. The system of claim 1, wherein the reservoir is a drug cartridge releasably received in a chamber proximate the first stored energy device.

3. The system of claim 1, wherein the drug cartridge comprises a piston and a septum proximate the openable end.

4. The system of claim 3, wherein the first stored energy device is operable to move the septum into contact with a piercing needle in fluid communication with the pathway.

5. The system of claim 3, wherein the first stored energy device is operable to drive the piston so as to transfer the fluid from the reservoir to the pathway.

6. The system of claim 3, wherein the first stored energy device comprises a first spring operable to drive the cartridge in a direction parallel to the array and a second spring operable to move the piston within the cartridge.

7. The system of claim 1, the system further comprising a second stored energy device coupled to the upper housing and in contact with the infusion device.

8. The system of claim 7, wherein the second stored energy device is operable to apply energy in a direction orthogonal to the major plane of the array, said energy applied to a surface of the infusion device remote from the array.

9. The system of claim 7, wherein the second stored energy device is operable to drive the infusion device at a velocity of at least 2 and no greater than about 20 m/sec.

10. The system of claim 7, wherein the second stored energy device is not attached to the infusion device.

11. The system of claim 7, wherein the first and second stored energy devices are comprised of at least one stored energy device from a group consisting of: spring devices, gaseous propellants, chemicals, electrical devices, and combinations thereof.

12. The system of claim 1, wherein the first stored energy device is actuatable to apply energy in a direction parallel to the major plane of the array.

13. The system of claim 1, wherein the infusion device comprises a releasable adhesive layer disposed on at least a portion of the attachment surface.

14. The system of claim 13, wherein the releasable adhesive layer is disposed on portion of a first major surface of the array.

15. The system of claim 14, wherein first stored energy device comprises a propellant canister, and wherein reservoir comprises a drug cartridge having a cylindrical housing, a piston, and a valve.

16. The system of claim 15, wherein the piston comprises a recess and wherein the canister is received in the recess.

17. The system of claim 1, wherein the first stored energy device is actuatable to transfer force in a certain direction along an axis perpendicular to the major plane of the array.

18. The system of claim 1, wherein the reservoir includes a transparent portion and infusion device includes a portion that allows for inspection of the transparent portion of the reservoir.

19. The system of claim 1, the system further including a second stored energy device, wherein the housing includes a single actuator operably connected to both the first and second stored energy devices and being actuatable to actuate the first and second stored energy devices.

20. The system of claim 1, wherein the infusion device comprises an actuator coupled to the first stored energy device.

21. The system of claim 1, wherein the array of hollow microneedles includes a spacing density of at least 3 and no greater than 18 microneedles per square centimeter.

22. The system of claim 1, wherein the upper housing is hingedly connected to the lower housing.

23. The system of claim 22, wherein the delivery apparatus comprises a second stored energy device, and wherein the second stored energy device is operable to direct an activation energy to the infusion device subsequent application of a force normal to a portion of the upper housing.

24. The system of claim 1, wherein the reservoir comprises a drug cartridge, wherein the cartridge is disposed in a recess in the infusion device, said recess located proximate the array along an axis perpendicular to the major plane of the array.

25. The system of claim 1, wherein the reservoir comprises a drug cartridge, and wherein the cartridge is disposed in a recess within the infusion device, said recess located proximate the array along an axis parallel to the major plane of the array.

26. The system of claim 1, wherein the infusion device comprises a height no greater than 2 cm.

27. A method comprising:
   providing the integrated system of claim 1,
   displacing the infusion device in a direction perpendicular to the major plane of the array;
   establishing fluid communication between the openable end of the reservoir and the pathway;
   detaching the infusion device from the housing; and
   forcing fluid from the reservoir into the microneedle array through the pathway.

28. The system of claim 1, wherein the lower housing comprises a base defining an opening.

29. The system of claim 1, wherein the infusion device is configured to provide for the reservoir replacement.

30. A system for delivering a microneedle array to a patient's skin surface, the system comprising:
   a delivery apparatus comprising a housing; and
   an infusion device detachably received in the housing, the infusion device including;
      a reservoir having a fluid therein and an openable end including a first major surface,
      a fluid pathway proximate the openable end, a first stored energy device proximate the reservoir actuatable to apply energy in a direction perpendicular to the first major surface, an attachment surface and an array of hollow microneedles coupled to a portion of the attachment surface, wherein the pathway is in fluid communication with the hollow microneedles, and a reservoir housing receiving the reservoir and the first stored energy source and the reservoir housing is between the reservoir and the housing wherein the housing is configured to provide for the infusion device replacement.

\* \* \* \* \*